United States Patent [19]

Müller et al.

[11] 4,400,300

[45] Aug. 23, 1983

[54] METHOD FOR RECOVERING AND REACTIVATING COBALT CATALYSTS USED IN THE REACTION OF OLEFINS WITH CARBON MONOXIDE AND ALKANOLS

[75] Inventors: Wolfgang H. E. Müller; Peter Hofmann, both of Marl, Fed. Rep. of Germany

[73] Assignee: Chemische Werke Hüls AG, Marl, Fed. Rep. of Germany

[21] Appl. No.: 256,384

[22] Filed: Apr. 22, 1981

[30] Foreign Application Priority Data

Apr. 30, 1980 [DE] Fed. Rep. of Germany ....... 3016653

[51] Int. Cl.$^3$ ......................... B01J 31/40; C07C 67/38
[52] U.S. Cl. ............................. 252/414; 260/410.9 R; 560/233
[58] Field of Search ........... 252/412, 413, 414, 431 N; 260/410.9 C; 560/233; 423/139; 75/119

[56] References Cited

U.S. PATENT DOCUMENTS 3,507,891  4/1970  Hearne et al. ............... 260/410.9 C
3,906,016  9/1975  Isa et al. ...................... 260/410.9 C
3,935,228  1/1976  Keblys ......................... 260/410.9 C

*Primary Examiner*—P. E. Konopka
*Attorney, Agent, or Firm*—Wells & Wells

[57] ABSTRACT

A process for recovering and reactivating catalysts used in the reaction of olefins with carbon monoxide and alkanols. The catalysts consist of a cobalt compound and pyridine, a non-ortho-substituted alkylpyridine or a mixture thereof as the promoter. The reacted mixture contains fatty acid ester, unconverted alkanol, uncoverted olefin, catalyst and promoter and this reacted mixture is treated with oxygen or an oxygenated gas at a temperature of about 20°–150° C. to oxidize the cobalt compound. The oxidized mixture is then separated by distillation to remove unconverted alkanol and olefin, the promoter, the reaction products and the distillation residue obtained thereby is mixed with pyridine, a non-ortho-substituted alkylpyridine or a mixture thereof. The suspension so obtained is treated with a mixture of carbon monoxide and hydrogen at a temperature of 100° to 250° C. and at a pressure of at least 50 bars.

4 Claims, No Drawings

METHOD FOR RECOVERING AND REACTIVATING COBALT CATALYSTS USED IN THE REACTION OF OLEFINS WITH CARBON MONOXIDE AND ALKANOLS

CROSS-REFERENCES TO RELATED APPLICATIONS

Applicants claim priority under 35 USC 119 for application P 30 16 653.1, filed Apr. 30, 1980 in the Patent Office of the Federal Republic of Germany.

The disclosure of coinventor Hofmann's copending application Ser. No. 125,482, filed Feb. 28, 1980 is incorporated herein to illustrate a process wherein the method of recovery of the present invention is applicable.

BACKGROUND OF THE INVENTION

The field of the invention is the recovery of catalysts used in the synthetic production of higher fatty esters.

The state of the art of the recovery of cobalt catalysts used in hydrocarboxylation may be ascertained by reference to U.S. Pat. Nos. 3,310,600; 3,507,891; 3,856,832; 3,906,016; and 4,041,057, the disclosures of which are incorporated herein.

It is known in the prior art that fatty acids can be prepared by reacting olefins with carbon monoxide and a compound containing a replaceable hydrogen atom, such as for instance, an alkanol, in the presence of a catalyst containing a metal of Group VIII of the Periodic Table of the elements and possibly containing also a promoter as disclosed by J. Falbe in "Synthesen mit Kohlenmonoxide" (Synthesizing with Carbon Monoxide), Springer publishers, Berlin, Heidelberg, New York, 1967.

A preferred embodiment of this reaction, which is termed hydrocarboxylation, is the reaction in the presence of cobalt catalysts. An especially preferred embodiment comprises the additional use of pyridine or of a non-ortho-substituted alkylpyridine as the promoter.

A substantial limitation of this homogeneously catalyzed reaction is the recovery of the relatively costly cobalt from the reaction mixture in a form permitting its renewed use as a catalyst.

A method described in West German Published Application No. 19 63 804 solves this problem by recovering the cobalt catalyst as the distillation sump substance and feeding it back as such into the reaction. Such a method, however, leads to losses of cobalt due to the separation of metallic cobalt in the reprocessing by distillation.

Such losses can be avoided in the method disclosed by U.S. Pat. No. 3,507,891 provided that the cobalt-catalyzed hydrocarboxylation is carried out in the presence of an alkylpyridine acting in a stabilizing manner in lieu of pyridine.

On the other hand, U.S. Pat. No. 3,906,016 discloses that such a method results neither in complete cobalt recovery nor does it make it possible to recycle the catalyst that would be free of degraded activity loss. The method of U.S. Pat. No. 3,906,016 avoids a separation of the metallic cobalt in the distillation reprocessing by carrying out the cobalt/pyridine or cobalt/alkylpyridine catalyzed reaction of olefin with alkanol and carbon monoxide in the presence of small amounts of water (0.1 to 2 moles/mole of olefin). In addition to esters, the corresponding fatty acids are thus formed in slight amounts. The conditions of reprocessing the reaction mixture by distillation leads to the formation of fatty acid cobalt compounds. Such thermally stable cobalt compounds are also formed when the reaction mixture is subjected to oxidizing treatment with air or oxygen before reprocessing.

Such a method, however, also has its limitations. Thus, the formation of fatty acids, which is constrained by the presence of water, leads to losses in the yield of the desired esters (the ester yields in part may drop down to 67%). The presence of water and fatty acids under the drastic conditions of hydrocarboxylation moreover leads to corrosion problems. Again, when paraffin diluted olefins are used, for instance, those prepared industrially by chlorinating/dechlorinating paraffins, the presence of water during the reaction results in demixing and hence to slowing the reaction. Lastly, this method also fails to make possible a complete conversion of the cobalt used into the desired fatty acid salt.

U.S. Pat. No. 3,856,832 discloses a further method for catalyst recovery. The process of this patent takes place in the presence of an excess of methanol as the esterification component, and a hydrocarbon is added to the reaction mixture at the end of reaction. In this manner, two phases are formed, of which the lowermost contains at least 95% of the cobalt used as catalyst. The lowermost phase containing the cobalt in active form then can be fed directly back into the hydrocarboxylation reaction.

The limitations of this method of U.S. Pat. No. 3,856,832 on the one hand consist in the restriction of the process to the production of methylesters, and on the other hand in the loss of the cobalt contained in the uppermost phase (up to 5% by weight).

In the method of U.S. Pat. No. 4,041,057, the cobalt remaining in the uppermost phase can be recovered by the process of U.S. Pat. No. 3,856,832 by burning the tarry residue obtained after its distillation reprocessing at temperatures from 1,000° to 4,000° F., by filtering the cobalt oxide so formed out of the combustion gases and by converting the cobalt oxide by means of carbon monoxide and hydrogen into cobalt carbonyl. This cobalt carbonyl can be fed back into the hydrocarboxylation.

While a complete recovery of the cobalt is possible with the combination of methods of U.S. Pat. Nos. 3,856,832 and 4,041,057, the profitability of such a procedure, however, is substantially reduced by the use of large amounts of hydrocarbons that appreciably affect the distillation reprocessing and by a costly, multistage recovery of the residual cobalt in the upper phase.

SUMMARY OF THE INVENTION

Having in mind the limitations of the prior art, it is an object of the present invention to create a generally applicable and economically implementable process for the recovery and reactivation of catalysts used in the reaction of olefins with carbon monoxide and alkanols where the catalyst is a cobalt compound and a promoter of pyridine, a non-ortho-substituted alkylpyridine or a mixture thereof is used.

This object has surprisingly been achieved by the following steps:

(a) after reacting olefins with carbon monoxide and alkanols in the presence of catalysts consisting of a cobalt compound and a promoter selected from the group pyridine, a non-ortho-substituted alkylpyridine or a mixture thereof to form a reaction mixture;

(b) the reaction mixture is treated with an oxygen containing gas to oxidize the cobalt compound;

(c) the unconverted alkanol and olefin, the promoter and the reaction products are removed by distillation;

(d) the cobalt distillation residue obtained thereby is absorbed in pyridine, non-ortho-substituted alkylpyridine or a mixture thereof and pyridine to form a suspension; and (e) the suspension is treated with a mixture of carbon monoxide and hydrogen at a temperature of about 100° to 250° C. and at a pressure of at least 50 bars and the cobalt distillation residue is directly converted back into an active form.

The surprise was that in view of the discussion of U.S. Pat. No. 4,041,057, Column 7, lines 60–64, it would not be expected that the combination of these critical process steps would make it possible to directly convert the cobalt residue back into an active form where the cobalt residue has been obtained in the distillation reprocessing.

DESCRIPTION OF THE PREFERRED EMBODIMENTS

In principle, the process of the present invention can be applied to all hydrocarboxylation processes for the production of fatty acid esters wherein a catalyst consisting of a cobalt compound and pyridine a non-ortho-substituted alkylpyridine or mixture thereof is being used as disclosed in the method of U.S. Pat. No. 3,507,891 and of U.S. patent application Ser. No. 125,482. Most importantly, the selection of the olefin used is not critical, that is, both straight chain and branched alpha olefins and also olefins with internal double bonds can be used. Moreover, olefins with more than one double bond and such with substituents, for intance, aryl groups, cyano groups, carboxymethyl groups and hydroxyl groups can also be used.

As a rule, olefins having 2 to 40, preferably having 4 to 20 C atoms are used and these are prepared by the state of the art methods. For instance, alpha-olefins are produced by oligomerizing ethylene a la Ziegler, as disclosed in German Patent 878,560 and U.S. Pat. No. 3,310,600, or by wax cracking, and olefins with internal double bonds are obtained by dehydrogenation or chlorination and ensuing dehydrochlorination of paraffins as disclosed in British Pat. No. 1,037,868.

In the method of British Pat. No. 1,037,868, blends of paraffins, that is, mixtures of different C-numbers, are used as a rule, so that the olefins obtained in turn also do not evince a uniform C number.

Further, these olefin mixtures contain in natural form the most imaginable isomeric forms. Besides the pure or possibly substituted olefins, it is also possible to use those having a paraffin content for instance up to 85%. The reason for the paraffin content is that the conversions obtained in the production of olefins are incomplete, and the unconverted paraffins are not separated, or are only incompletely separated.

In addition to the olefin used being not critical, the kind of alkanol which is being reacted with the olefin and the carbon monoxide also is not critical. As a rule, alkanols having 1 to 20, preferably 1 to 4 C atoms, are used. Typical representatives from the group of primary alcohols are for instance methanol, ethanol, propanol-(1) and butanol-(1).

The kind of cobalt used in the hydrocarboxylation also is not material. Cobalt carbonyls, for instance dicobaltoctacarbonyl, are just as suited as carboxylic acid cobalt salts, for instance cobalt acetate, cobalt naphthenate and cobalt-2-ethylhexanoate, and salts of cobalt with inorganic acids, such as cobalt nitrate and cobalt sulfate. Preferably those carboxylic acid cobalt salts are used, of which the anions correspond to the acid group of the fatty acid esters formed in the hydrocarboxylation.

Besides pyridine alone or in a mixture, suitable promoters are all non-ortho-substituted alkylpyridines, for instance 3-picoline and 4-picoline, 3,4-lutidine and 3,5-lutidine, and 3-ethylpyridine and 4-ethylpyridine.

Lastly, the reaction conditions having been applied to the hydrocarboxylation are without significance for the further processing of the present invention. As a rule, the hydrocarboxylation processes are carried out at temperatures of 80° to 300°, preferably 150° to 220° C., and at carbon monoxide pressures of 10 to 800, preferably 100 to 300 bars.

What is process-critical to the present process, however, is the oxidizing treatment of the reaction mixture prior to the cobalt recovery, using oxygen or a gas containing oxygen, preferably air, at temperatures of 20° to 150°, preferably 50° to 120° C. This treatment, which already was described in U.S. Pat. No. 3,507,891, Column 4, lines 21–43, and U.S. patent application Ser. No. 125,482, which is not yet part of the state of the art, is carried out until the cobalt compounds, which in the ensuing distillation-reprocessing result in the separation of metallic cobalt, are destroyed.

In a preferred embodiment of the invention disclosed in application Ser. No. 125,482, the reaction mixture is treated at a temperature between about 20° and 100° C., preferably air, until the cobalt compounds which result in the separation of metallic cobalt during the processing by distillation are destroyed by oxidation. This embodiment can be carried out for instance in a trickling column by circulating the oxygenated gas in counterflow to the reaction discharge. The destruction by oxidation is easily recognized in the change in color (from brown-orange to brown-violet).

In the ensuing distillation-reprocessing, the unconverted alkanol and olefin, the promoter and the reaction products are separated at sump temperatures up to 350° C. Step-wise reprocessing is preferred, as thereby fractions are obtained which, except for the fatty acid esters, can be fed back into the process at a suitable location.

The tarry sump product with a cobalt content of about 2 to 30, preferably 4 to 15% by weight remaining from the reprocessing by distillation is absorbed in the pyridine or non-ortho-substituted alkylpyridine used as promoters. This can be implemented for instance by introducing the sump product, which already becomes fluid at about 50° C., into an agitated vessel loaded with the promoter. The amount of promoter is so selected that the promoter/cobalt ratio required for the hydrocarboxylation reaction shall not be exceeded. A preferred implementation of the process of the present invention consists more than any other approach in using the promoter separated by distillation from the reaction mixture to absorb the cobalt residue, and in compensation for any losses by adding fresh promoter.

As a rule, gas mixtures having 10 to 90, preferably 40 to 60% by volume of hydrogen are used to treat the suspension, so obtained, with the mixture of carbon monoxide and hydrogen.

The treatment temperature is between about 100° and 250° C., preferably between 120° and 200° C., and the total pressure must be at least 50 bars. An upper critical limit on the total pressure is determined not by the chemical course of the process, but by the pressure resistance of the available equipment. Preferably the pressure ranges from about 100 to 400 bars.

The duration of treatment can be easily ascertained by trial and error. It depends mostly on the selected conditions of temperature and pressure, and as indicated by experience, ought to be at least 5 minutes.

Success in treatment can be recognized on one hand in that the solids contained in the suspension used were dissolved, and on the other hand that the catalytic solution so obtained is active again.

The treatment of the cobalt suspension with the mixture of carbon monoxide and hydrogen is carried out for instance in a pressure vessel, a cascade of pressure vessels or a tubular reactor.

The examples below illustrate the process of the present invention in further detail.

EXAMPLE 1

(a) A mixture of 1,660 g of alpha-dodecane and 640 g of methanol is reacted in the presence of 59 g of cobalt tridecanoate (cobalt content 10%) catalyst and 279 g of gamma-picoline promoter with carbon monoxide (containing 2% by volume of hydrogen) at a total pressure of 250 bars and a temperature of 170° C. in a 5-liter agitating autoclave (stainless steel). The reaction is stopped after one hour by rapid cooling.

The gas-chromatographic analysis of the mixture of reaction (1st batch) shows 35% dodecene and 65% reaction products consisting of 98% of tridecanoic acid methylester with an n-proportion of 83%.

The reaction mixture is treated in a trickling column (length: 200 cm; diameter: 4 cm) filled with 4×4 mm Raschig rings at normal pressure and 50° C. with air in counterflow. 2 Liters of the reaction mixture are supplied per hour from above and the air flow is 100 liters/hr. Organic components entrained by the air are condensed by a condenser at the head of the trickling column.

The reaction mixture so produced is decomposed by distillation into a fraction of methanol, olefin, gamma-picoline and ester. 65 g of a tarry residue containing the catalytic metal used, remain as the sump product.

(b) The above residue is absorbed in 279 g of gamma-picoline (274 g from the recovered gamma-picoline and 5 g of fresh gamma-picoline) and treated for 0.3 hours at 200 bars and 170° C. with synthesis gas (50% by volume carbon monoxide, 50% by volume hydrogen) in the 5-liter V4A agitator autoclave. This is followed by quick cooling and expansion to 1 bar.

After adding 1,660 g of alpha-dodecane and 640 g of methanol to the catalytic solution and applying 150 bars of carbon monoxide (containing 2% by volume of hydrogen), the temperature of the substance is quickly raised to 170° C. The time of reaction is 1 hour, during which the total pressure is kept at 250 bars by replenishing carbon monoxide.

The gas-chromatographic analysis of the reaction mixture (2nd batch) shows 33% of dodecane and 67% of reaction products consisting of 97% of tridecanoic acid methylester with an n-proportion of 82.5%.

Following treatment of the reaction output with air and separation by distillation of ethanol, olefin, gamma-picoline and ester (the conditions are the same as in 1a), 67 g of a tarry residue are obtained as the sump product.

(c) The residue obtained from the second reaction (Example 1b) is treated again under the conditions of Example 1b and then used for synthesizing tridecanoic acid methylester under the conditions of Example 1b.

The gas-chromatographic analysis of the reaction mixture (3rd batch) shows 34% of dodecane and 66% of reaction products consisting of 97% tridecanoic acid methylester with an n-proportion of 84%.

COMPARISON EXAMPLE 65 g of a tarry reside containing the catalytic metal and obtained as the distillation sump product as in Example 1a are used without being treated with synethetic gas under the conditions of Example 1a again as a catalyst in the preparation of tridecanoic acid methylester.

The gas-chromatographic analysis of the reaction mixture, which at room temperature (20° C.) contains solids, evinces 45% of dodecene and 55% of reaction products consisting of 97% tridecanoic acid methylester with an n-proportion of 82%.

The reaction mixture is reprocessed as in Example 1a and the tarry residue obtained thereby is used again, without treatment with synthesis gas, as a catalyst. The reaction carried out under the conditions of Example 1a provides a reaction mixture containing solids which by gas-chromatography evinces 56% of dodecene and 34% of reaction products containing 96% tridecanoic acid methylester with an n-proportion of 83%.

COMPARISON EXAMPLE B

A reaction product obtained as in Example 1a is reprocessed without prior treatment with air in a trickling column by means of distillation. Cobalt deposits in the distillation flask (cobalt mirror), and an ester fraction with a cobalt content of 13 ppm is obtained. The tarry sump substance (66 g) remaining as distillation residue following pre-treatment with synthesis gas is again used in the preparation of tridecanoic acid methylester under the conditions of Example 1b.

The gas-chromatographic analysis of the reaction mixture evinces 40% dodecene and 60% reaction products containing 98% tridecanoic acid methylester with an n-proportion of 82%.

COMPARISON EXAMPLE C

Comparison Example B is repeated except that the treatment with the synthesis gas is omitted when again the distillation residue containing the catalytic metal is used.

A reaction mixture is obtained, with solids suspended in it, and which by gas-chromatographic analysis contains 48% dodecene and 52% reaction products consisting of 97% tridecanoic acid methylester with an n-proportion of 84%.

EXAMPLES 2-9

Example 1 is repeated except that other conditions are selected to treat the tarry distillation residue containing the catalytic metal with carbon monoxide/hydrogen. The results are summarized in Table 1.

EXAMPLES 10-16

Examples 1a and 1b are repeated, except that other conditions are selected for the treatment of reaction mixture with oxygenated gases. The results are summarized in Table 2.

EXAMPLE 17

Examples 1a and 1b are repeated except that in lieu of alpha-dodecene, a statistical mixture of linear dodecenes with internal double-bonds is used, and the following molar ratios of the input materials are used:

olefin/methanol/gamma-picoline/cobalt (used as 10% cobalt naphthenate)=1/2/0.4/0.04.

The reaction results are in Table 3.

EXAMPLE 18

Example 17 is repeated with a statistical mixture of linear dodecenes and tridecenes (80% by weight of $C_{12}$; 20% by weight of $C_{13}$) with internal double-bonds (alpha proportion less than 1%) as the input olefin.
The reaction results are listed in Table 3.

EXAMPLE 19

Example 17 is repeated with a statistical mixture of linear decenes and undecenes (10% by weight $C_{10}$; 90% by weight $C_{11}$) with internal double-bonds (alpha proportion is less than 1%), which for 1 part by weight of olefin mixture contains 3 parts by weight of a mixture of decane and undecane (10% by weight $C_{10}$; 90% by weight $C_{11}$). The following molar ratios of the input substances are selected:

olefin (100%)/methanol/gamma-picoline/cobalt (used as 10% cobalt naphthenate)=1/5/1/0.1.

The test results are shown in Table 3.

EXAMPLE 20

Example 17 is repeated except that the cobalt naphthenate is replaced by the same molar amount of cobalt acetate. The reaction results are in Table 3.

EXAMPLE 21

Example 17 is repeated except that the cobalt naphthenate is replaced by the equivalent molar amount of dicobalt octacarbonyl.
The reaction results are in Table 3.

EXAMPLE 22

Example 17 is repeated except that the gamma-picoline is replaced by the same molar amount of pyridine. The reaction results are shown in Table 3.

TABLE 1

Treatment Conditions of Distillation Residue

| Example No. | Pressure bar | Temperature °C. | Duration of Reaction h | CO/H₂ Composition CO Vol-% | H₂ Vol-% |
|---|---|---|---|---|---|
| 2 | 140 | 170 | 0.3 | 50 | 50 |
| 3 | 280 | 170 | 0.3 | 50 | 50 |
| 4 | 200 | 190 | 0.3 | 50 | 50 |
| 5 | 200 | 140 | 0.3 | 50 | 50 |
| 6 | 200 | 170 | 0.15 | 50 | 50 |
| 7 | 200 | 170 | 1.0 | 50 | 50 |
| 8 | 200 | 170 | 0.3 | 75 | 25 |
| 9 | 200 | 170 | 0.3 | 25 | 75 |

Reaction Results

| Example No. | 2nd Batch Conversion % | Selectivity % | n-Proportion % | 3rd Batch Conversion % | Selectivity % | n-Proportion % |
|---|---|---|---|---|---|---|
| 2 | 63 | 98 | 83 | 64 | 97.5 | 83.5 |
| 3 | 65 | 97.5 | 84 | 64 | 98 | 83 |
| 4 | 66 | 98.5 | 83 | 65 | 98 | 84 |
| 5 | 64 | 98 | 84 | 63 | 97 | 83 |
| 6 | 65 | 98 | 82.5 | 64 | 98.5 | 82.5 |
| 7 | 63 | 97 | 83 | 63 | 98 | 82.5 |
| 8 | 67 | 98 | 84 | 65 | 97.5 | 83 |
| 9 | 65 | 98.5 | 83 | 65 | 98 | 83.5 |

TABLE 2

| | Treatment Conditions of Reaction Mixture | | | | | Reaction Results 2nd Batch | | |
|---|---|---|---|---|---|---|---|---|
| Example No. | Pressure bar | Temperature °C. | Liquid Flow Rate l/h | Gas Flow Rate l/h | Gas Composition Vol. % | Conversion % | Selectivity % | n-Proportion % |
| 10 | 1 | 40 | 2 | 100 | air | 65 | 98 | 84 |
| 11 | 1 | 80 | 2 | 100 | air | 64 | 97 | 83 |
| 12 | 15 | 60 | 2 | 100 | air | 64.5 | 97 | 83 |
| 13 | 1 | 60 | 5 | 100 | O₂ | 64 | 98 | 83 |
| 14 | 1 | 60 | 2 | 150 | air | 64 | 98.5 | 83.5 |
| 15 | 1 | 60 | 1 | 50 | air | 65 | 98 | 83.5 |
| 16 | 1 | 60 | 2 | 100 | Ar(50),O₂(50) | 65 | 97.5 | 84 |

TABLE 3

| Example No. | Reaction Results from 1st Batch Conversion % | Selectivity % | n-Proportion % | Reaction Results from 2nd Batch Conversion % | Selectivity % | n-Proportion % |
|---|---|---|---|---|---|---|
| 17 | 52 | 97 | 78 | 53 | 96 | 78 |
| 18 | 50 | 96.5 | 77 | 48 | 97 | 78 |
| 19 | 42 | ≦97 | 82 | 42 | ≦97 | 81.5 |
| 20 | 50 | 97.5 | 79 | 53 | 97 | 78 |
| 21 | 53 | 97 | 77 | 52 | 97 | 78 |
| 22 | 48 | 98 | 73 | 48 | 97.5 | 74 |

We claim:

1. In a process for preparing an alkylester of a saturated aliphatic carboxylic acid by reacting olefin with alkanol in the presence of a catalyst consisting of a cobalt compound and a promoter selected from the group consisting of pyridine, non-ortho-substituted alkylpyridine, and mixtures thereof to form a reaction mixture, the improvement comprising reactivating and recovering said catalyst by:

(a) treating said reaction mixture with a gas containing oxygen and forming an oxidized cobalt compound;

(b) carrying out a distillation and removing unconverted olefin, uncoverted alkanol, promoter and reaction products and producing a distillation residue containing said oxidized cabalt compound;

(c) mixing an additional portion of said promoter with said distillation residue to form a suspension; and (d) treating said suspension with a mixture of carbon monoxide and hydrogen at a temperature of about 100° to 250° C. and at a pressure of at least 50 bars, to reactivate said catalyst, and recovering said reactivated catalyst.

2. The process of claim 1, wherein promoter separated by distillation from the reaction mixture is recycled and mixed with said cobalt distillation residue.

3. The process of claim 1, wherein mixtures of carbon monoxide and hydrogen are used, which contain from 10 to 90% by volume of hydrogen.

4. The process of claim 1, wherein step (a) is carried out at a temperature of about 20° to 150° C.

* * * * *